(12) United States Patent
Pouteau et al.

(10) Patent No.: US 10,966,645 B2
(45) Date of Patent: Apr. 6, 2021

(54) DEVICE FOR TAKING A LIQUID SAMPLE BY CAPILLARITY AND ASSOCIATED ANALYSIS METHOD

(71) Applicant: COMMISSARIAT A L'ENERGIE ATOMIQUE ET AUX ENERGIES ALTERNATIVES, Paris (FR)

(72) Inventors: Patrick Pouteau, Meylan (FR); Jean Berthier, Meylan (FR); Vincent Poher, Guines (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 730 days.

(21) Appl. No.: 14/773,215

(22) PCT Filed: Mar. 6, 2014

(86) PCT No.: PCT/EP2014/054380
§ 371 (c)(1),
(2) Date: Sep. 4, 2015

(87) PCT Pub. No.: WO2014/135652
PCT Pub. Date: Sep. 12, 2014

(65) Prior Publication Data
US 2016/0022189 A1    Jan. 28, 2016

(30) Foreign Application Priority Data

Mar. 7, 2013    (FR) .................................. 1352050

(51) Int. Cl.
*A61B 5/15*    (2006.01)
*A61B 10/00*    (2006.01)
(Continued)

(52) U.S. Cl.
CPC ........ *A61B 5/150755* (2013.01); *A61B 5/151* (2013.01); *A61B 5/150022* (2013.01);
(Continued)

(58) Field of Classification Search
CPC .......... A61B 5/150755; A61B 5/14532; A61B 5/151; A61B 10/0045; A61B 5/150022;
(Continued)

(56) References Cited

U.S. PATENT DOCUMENTS 3,363,503 A   1/1968  Shifrin
4,088,448 A   5/1978  Lilja et al.
(Continued)

FOREIGN PATENT DOCUMENTS

EP    0388170 A2    9/1990
EP    0821784 A1    2/1998
(Continued)

OTHER PUBLICATIONS

U.S. Appl. No. 10/576,345, filed Oct. 23, 2006, US2007-0207055 A1, Gilles Marchand, et al.
(Continued)

*Primary Examiner* — Patrick Fernandes
(74) *Attorney, Agent, or Firm* — Oblon, McClelland, Maier & Neustadt, L.L.P.

(57) ABSTRACT

A device for taking a sample of liquid by capillarity, including a channel for flow of the liquid delimited by two internal walls of the device between which a channel bottom extends, the distance separating the two internal walls decreasing in the direction of the channel bottom, the channel extending between a first collecting end, open onto outside of the device and configured to receive the liquid, and a second end, to enable the liquid to flow by capillarity along the channel bottom from the first end towards the second end. The channel includes, at the second end, a
(Continued)

blocking structure to block the flow of liquid in the channel from the first end towards the second end.

21 Claims, 12 Drawing Sheets

(51) Int. Cl.
  *B01L 3/00* (2006.01)
  *A61B 5/151* (2006.01)
  *A61B 5/157* (2006.01)
  *G01N 1/10* (2006.01)

(52) U.S. Cl.
  CPC .... *A61B 5/150068* (2013.01); *A61B 5/15105* (2013.01); *A61B 5/15142* (2013.01); *A61B 5/150358* (2013.01); *A61B 5/150412* (2013.01); *A61B 5/150503* (2013.01); *A61B 10/0045* (2013.01); *B01L 3/5027* (2013.01); *A61B 5/157* (2013.01); *A61B 5/150251* (2013.01); *A61B 5/150419* (2013.01); *A61B 5/150748* (2013.01); *B01L 2200/0684* (2013.01); *B01L 2300/161* (2013.01); *B01L 2400/0406* (2013.01); *G01N 1/10* (2013.01)

(58) Field of Classification Search
  CPC ........ A61B 5/150068; A61B 5/150358; A61B 5/150412; A61B 5/150503; A61B 5/15105; A61B 5/15142; A61B 5/0251; A61B 5/157; B01L 3/5027
  See application file for complete search history.

(56) References Cited

U.S. PATENT DOCUMENTS

| | | | |
|---|---|---|---|
| 4,957,582 A | 9/1990 | Columbus | |
| 5,200,248 A * | 4/1993 | Thompson | B29C 47/12 428/119 |
| 5,674,457 A | 10/1997 | Williamsson et al. | |
| 5,753,514 A | 5/1998 | Karlsson et al. | |
| 6,612,111 B1 | 9/2003 | Hodges et al. | |
| 7,595,925 B2 | 9/2009 | Valette et al. | |
| 7,829,271 B2 | 11/2010 | Delattre et al. | |
| 8,075,754 B2 | 12/2011 | Sauter-Starace et al. | |
| 8,216,827 B2 | 7/2012 | Pouteau et al. | |
| 8,349,158 B2 | 1/2013 | Sauter-Starace et al. | |
| 8,563,325 B1 * | 10/2013 | Bartsch | B01L 3/502776 422/502 |
| 8,673,153 B2 | 3/2014 | Campagnolo et al. | |
| 2002/0177788 A1 | 11/2002 | Hodges et al. | |
| 2003/0018282 A1 * | 1/2003 | Effenhauser | A61B 5/1411 600/583 |
| 2004/0096358 A1 * | 5/2004 | Blankenstein | B01L 3/50273 422/520 |
| 2004/0236250 A1 | 11/2004 | Hodges et al. | |
| 2005/0010137 A1 | 1/2005 | Hodges et al. | |
| 2006/0000238 A1 * | 1/2006 | Griffin | G01N 30/52 65/31 |
| 2006/0110283 A1 * | 5/2006 | Fish | G01N 21/03 422/52 |
| 2006/0203236 A1 | 9/2006 | Ji et al. | |
| 2006/0203237 A1 | 9/2006 | Ji et al. | |
| 2007/0017805 A1 | 1/2007 | Hodges et al. | |
| 2007/0105210 A1 | 5/2007 | Delattre et al. | |
| 2007/0207055 A1 | 9/2007 | Marchand et al. | |
| 2007/0276193 A1 | 11/2007 | Rivera et al. | |
| 2008/0081976 A1 | 4/2008 | Hodges et al. | |
| 2009/0267167 A1 | 10/2009 | Pouteau et al. | |
| 2010/0189601 A1 * | 7/2010 | Crawford | B01F 5/0646 422/69 |
| 2010/0276005 A1 | 11/2010 | Allain et al. | |
| 2014/0001116 A1 | 1/2014 | Berthier et al. | |
| 2014/0037515 A1 | 2/2014 | Charles et al. | |
| 2014/0283367 A1 | 9/2014 | Berthier et al. | |

FOREIGN PATENT DOCUMENTS

| | | |
|---|---|---|
| EP | 1701149 A1 | 9/2006 |
| FR | 2325920 A1 | 4/1977 |
| WO | 95/10357 A1 | 4/1995 |
| WO | 01/72220 A1 | 10/2001 |

OTHER PUBLICATIONS

U.S. Appl. No. 10/577,274, filed Nov. 6, 2006, US2007-0105210 A1, Cyril Delattre, et al.
U.S. Appl. No. 12/441,371, filed Mar. 13, 2009, US2009-0267167 A1, Patrick Pouteau, et al.
U.S. Appl. No. 12/766,231, filed Apr. 23, 2010, US2010-0276005 A1, Marjolaine Allain, et al.
U.S. Appl. No. 14/110,603, filed Oct. 8, 2013, US2014-0037515 A1, Raymond Charles, et al.
U.S. Appl. No. 10/580,453, filed Mar. 23, 2006, US2007-0276193 A1, Florence Rivera, et al.
U.S. Appl. No. 14/001,425, filed Aug. 23, 2013, US2014-0001116 A1, Jean Berthier, et al.
U.S. Appl. No. 14/221,402, filed Mar. 21, 2014, US2014-0283367 A1, Jean Berthier, et al.
International Search Report dated Apr. 8, 2014 in PCT/EP2014/054380 filed Mar. 6, 2014.
French Search Report dated Jan. 24, 2014 in FR 1352050 filed Mar. 7, 2013.

* cited by examiner

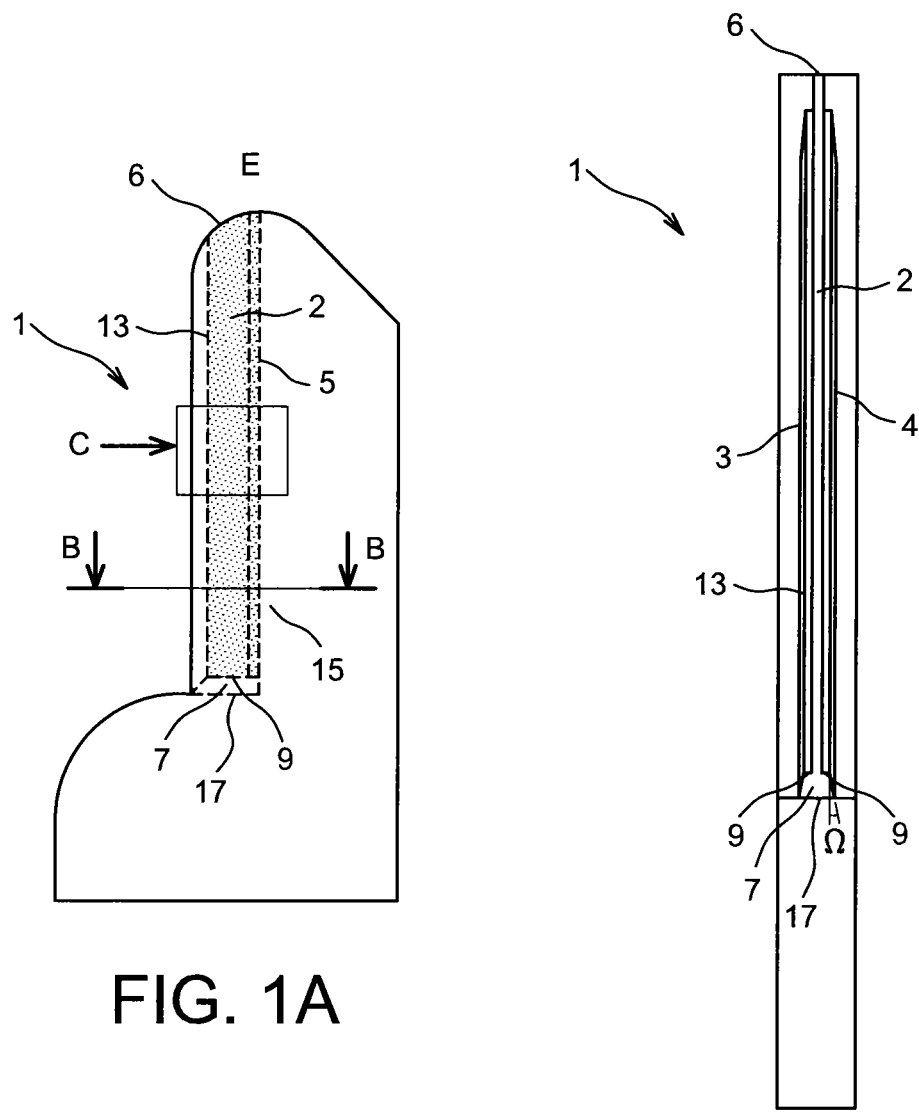
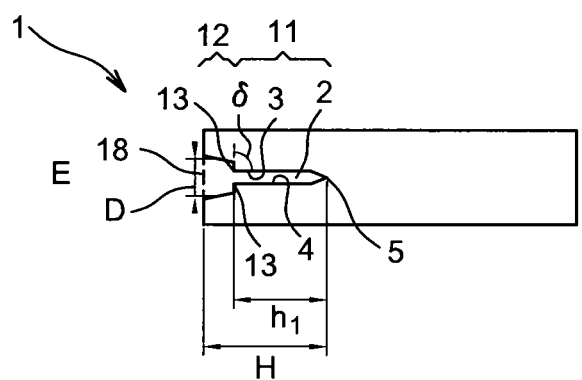
FIG. 1A
FIG. 1B
FIG. 1C

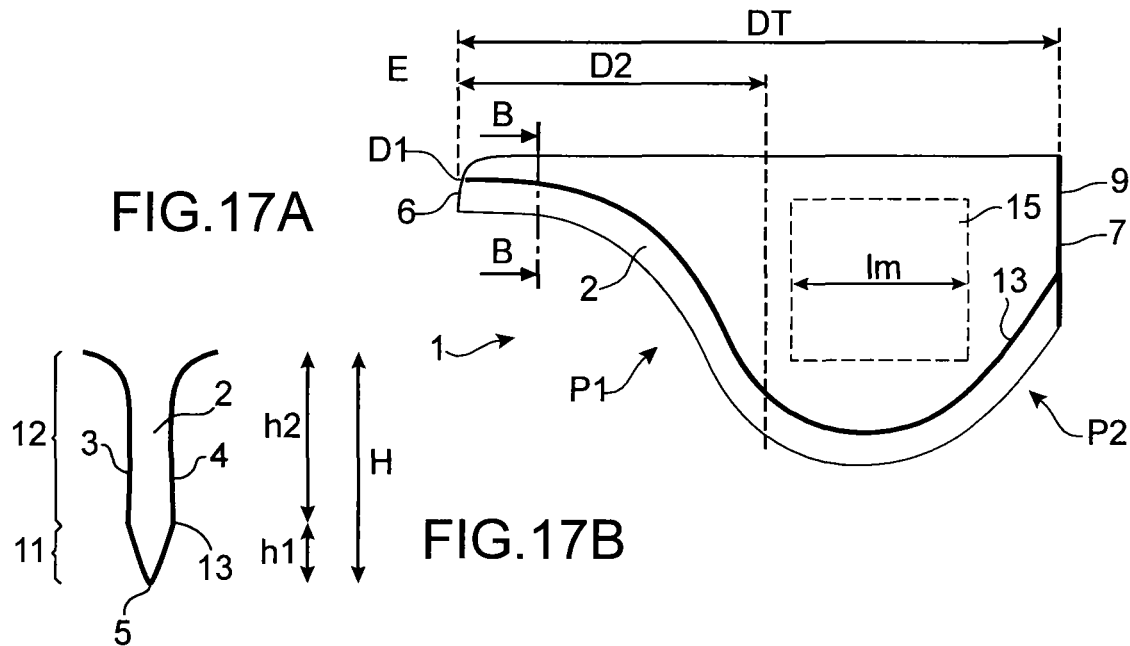
FIG.17A
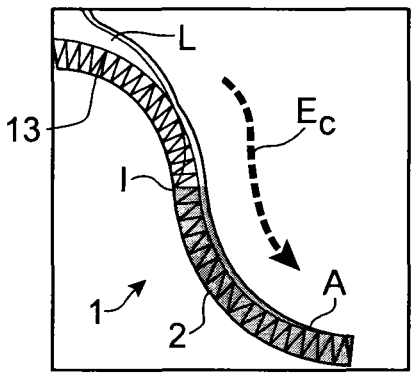
FIG.17B
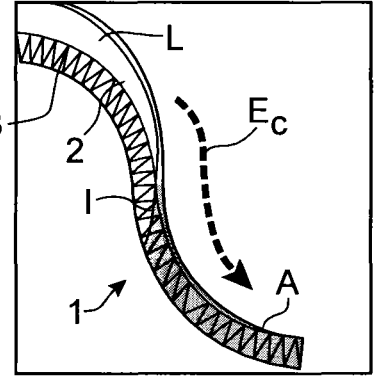
FIG.18A
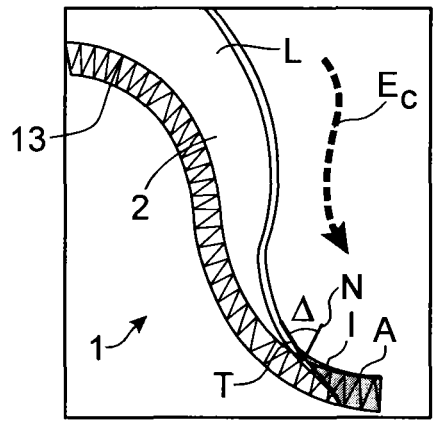
FIG.18D
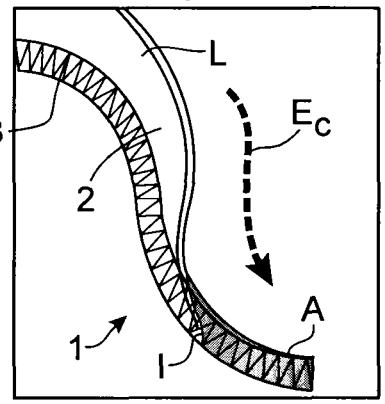
FIG.18B
FIG.18C

DEVICE FOR TAKING A LIQUID SAMPLE BY CAPILLARITY AND ASSOCIATED ANALYSIS METHOD

TECHNICAL FIELD

The present invention relates to the field of devices for collecting liquid samples, in particular chemical and/or biological samples, intended to be analysed. It relates in particular to the field of devices for sampling liquid by capillarity.

The invention thus proposes a device for taking a sample of liquid by capillarity and a method for analysing a liquid sample taken by means of such a device.

PRIOR ART

Numerous devices capable of sampling liquid intended to be analysed are known in the prior art.

For example, test devices are known in the form of paper strips functionalised with reagents necessary to the performance of tests. The liquid sample is then put in contact with one end of the strip and, under the effect of the porosity of the paper and capillary forces, the liquid gradually fills the strip. Then a reagent present on the strip in dried or lyophilised form mixes with the liquid in the course of the filling and the reaction caused can enable the liquid sample to be analysed.

The European patent EP 0 821 784 B1 also describes another type of device for collecting a liquid sample intended to be analysed. This device comprises a fluid microchannel for flow of the liquid having a capillary force greater than that of an analysis bowl situated between the fluid microchannel and a cavity giving onto the outside of the device. The fluid microchannel emerges on a first end enabling liquid to be collected and a second end open to the outside.

However, the implementation of these solutions is known from the prior art disclosed above, and in particular the one described in European Patent EP 0 821 784 B1, raises several constraints.

For example, the device described in European patent EP 0 821 784 B1 has, in use, a drawback in terms of risk of contamination of the outside of the device by the sampled liquid. This is because the fluid microchannel is open onto the outside at both ends and, when a liquid is introduced into the device, the liquid fills the fluid microchannel and the analysis bowl but may also flow towards the outside, in particular through the second end open onto the outside. In particular, this may occur because of the inertia force applied to the liquid filling the fluid microchannel. In addition, the liquid is not sufficiently maintained inside the zone formed by the fluid microchannel and the analysis bowl and it may happen that the liquid also flows outside the device by means of the cavity.

Furthermore, where a deposit of reagent in the microchannel is required, the configuration of this device is not really suitable for obtaining a homogeneous deposit of the reagent in the microchannel. Because of the narrowness and the depth of the fluid microchannel, it is in fact difficult to deposit or dry a reagent homogeneously.

Moreover, the form of the generatrix of the microchannel of this device, that is to say the form of the direction in which the microchannel extends, may accentuate the formation of undesirable air bubbles in the device when the liquid is sampled.

Finally, the configuration of the first end of the microchannel used for collecting the liquid to be analysed is not satisfactory for allowing optimum efficiency of the sampling and facilitating the collection operation.

DISCLOSURE OF THE INVENTION

There exists a need for proposing an alternative to the known devices of the prior art for collecting a liquid sample, in particular chemical and/or biological, to analyse it.

There exists in particular a need for designing a device for taking such a liquid sample that can enable the liquid to be confined in order to prevent at least part of the sample liquid escaping outside the device.

There also exists a need for making it possible, if necessary, to carry out a substantially homogeneous deposition of a reagent in the device, intended to come into contact with the sampled liquid, in order to achieve in particular better analysis results, in particular in the case of analyses measured by optical signal where the homogeneity of the result is a quality criterion.

There also exists a need for reducing, or even preventing, the formation of undesirable air bubbles in the device when a liquid sample is taken.

Finally, there exists a need for improving and facilitating the ergonomics and efficiency of the sampling device when the liquid sample is collected.

The aim of the invention is to at least partially remedy the requirements mentioned above and the drawbacks relating to the embodiments of the prior art.

The subject matter of the invention is thus, according to one of its aspects, a device for taking a liquid sample by capillarity, comprising a channel for flow of the liquid delimited by two internal walls of the device, between which a channel bottom lies, the distance separating the two internal walls decreasing in the direction of the channel bottom, the channel extending between a first collecting end, open to the outside of the device and able to receive the liquid, and a second end, so as to enable the liquid to flow by capillarity along the channel bottom from the first end towards the second end.

Advantageously, the channel comprises, at the second end, a blocking means able to block the flow of liquid in the channel from the first end towards the second end. This blocking means blocks the flow of liquid or slows it down.

By virtue of this feature of the invention, it can be possible to fill the channel of the device with the liquid sample taken by capillary effect while greatly reducing, or even completely preventing, the risk of overflow of liquid outside the device by virtue of the presence of the blocking means. It is thus possible to achieve a confinement of the liquid sample in the device and to prevent the risk of contamination of the outside environment by liquid coming from the device.

The device according to the invention may also comprise one or more of the following features taken in isolation or in accordance with all possible technical combinations.

The device may be used for analysing liquid samples (or volumes of liquid) taken by means of it. In particular, the device may be used in the field of in vitro diagnostic testing, and in particular for biological tests carried out close to a patient, thus making it possible to relocate the analysis outside an analysis laboratory and to carry it out close to the patient. For this purpose, the device may be designed so as to be a disposable consumable, after analysis by means of instrumentation for suitable reading of the device.

The liquid to be sampled for analysis may be of any type, being in particular a biological liquid, in particular a bodily fluid such as blood, urine, sweat, lachrymal fluid, lymphatic liquid or sperm, among other things.

The liquid may be analysed by suitable analysis means, in particular optical analysis means. These analysis means may be disposed on either side of the channel. In other words, the device may for example be inserted in an analysis means so as to permit analysis of the liquid contained in the channel.

The liquid may also be analysed by electrical analysis means. These analysis means may in particular comprise electrodes, integrated for example on an internal wall.

An analysis zone or zone of interest, in particular an optical measuring zone, may be defined on the channel to enable the liquid to be analysed. For example, in the context of an optical analysis, the analysis zone may be illuminated by a light beam and an optical sensor for generating an image of the zone analysed, the processing of this image giving information on at least one parameter of the analysed liquid.

The blocking means slows down or even stops the flow of liquid in its flow progress from the first end towards the second end of the channel.

The blocking means may be of various types. For example, the channel may comprise a blocking means in the form of a wall closing off the channel. The closure wall may in particular be situated at the second end of the channel, extending in particular between the two internal walls of the device. The closure wall may thus close off the channel and block any flow of liquid beyond it.

The channel may also comprise a blocking means in the form of at least one blocking ridge formed on at least one internal wall (or lateral wall) of the device, allowing a broadening of at least part of the channel. In other words, the width of at least part of the channel may increase downstream of the blocking ridge considering the flow of liquid from the first end towards the second end. The blocking ridge may in particular allow a broadening of the bottom of the channel.

The blocking ridge may be situated upstream of the second end considering the flow of liquid from the first end towards the second end.

Preferably, the channel may comprise two blocking ridges situated on each internal wall. The two blocking ridges may be disposed substantially facing each other, that is to say situated on the internal wall substantially at the same height of the channel.

The broadening of the channel may depend on the angle formed by the blocking ridge with the internal wall of the device in the case of non-broadening. Thus, in the case of non-broadening (no blocking ridge present), this angle is zero. In the case of broadening, the blocking ridge may form an angle greater than 20°, preferably greater than 50°, or even 60°, or even more preferably between 80° and 100°. The liquid may then attach to this blocking ridge, which blocks the advance of the liquid in the channel.

Moreover, the channel may also comprise a blocking means in the form of a coating made locally hydrophobic in order to prevent the flow of liquid.

The coating may in particular be situated at the bottom of the channel and/or at least one internal wall, for example the two internal walls.

The channel may also comprise a blocking means in the form of a broadening, in particular gradual, of the channel bottom, able to reduce the capillary force applied to the liquid, when the latter progresses towards the second end.

Furthermore, the channel may be divided into at least a lower part comprising the channel bottom and an upper part so that the lower part is situated between the channel bottom and the upper part. The lower and upper parts are delimited by the internal walls.

The lower and upper parts communicate with each other.

The lower part has a capillary force higher than that of the upper part so as to allow a spontaneous capillary flow (SCF) of the liquid along the channel bottom from the first end towards the second end.

The lower part may thus form a microchannel for flow of the liquid or a fluid finger for flow of the liquid joining the channel bottom and then progressing from the first end towards the second end.

The width of the upper part is advantageously greater than that of the bottom part. In other words, the upper part may constitute a broadening of the lower part.

The separation between the lower and upper parts of the channel may be achieved by means for anchoring the liquid on at least one internal wall of the device, allowing a blockage of the flow of liquid from the lower part towards the upper part.

The anchoring means enable the liquid to be confined inside the lower part of the channel. In other words, the anchoring means can hold the liquid in the lower part below a predetermined height of the channel.

Advantageously, each internal wall comprises means for anchoring the liquid. The anchoring means of each internal wall may be disposed substantially facing each other. In order words, the anchoring means of each internal wall can be situated substantially at the same height of the channel.

The anchoring means may comprise anchoring ridges. The anchoring ridges may delimit the narrow zone of the lower part from the wide zone of the upper part.

In one embodiment of the lower part of the channel in which the channel bottom extends perpendicularly between the internal walls, the spontaneous capillary flow SCF in the lower part of the channel can be obtained when the following relationship is satisfied:

$$d_1/(d_1+2h_1)<\cos\theta$$

where $d_1$ is the width of the lower part, $h_1$ is the height of the lower part, and $\theta$ is the wetting angle of the liquid on the material constituting the internal wall, that is to say the angle formed by a drop of liquid with the material at its triple line. The greater this angle, the more hydrophilic the liquid.

For the spontaneous capillary flow to be able to occur, it is in any event necessary for the lower part to be sufficiently narrow. In particular, the width $d_1$ of the lower part may be less than or equal to 1 mm, or even 500 μm, preferably between 30 μm and 500 μm, or even between 100 μm and 200 μm, in particular when the liquid sample is blood.

The width of the upper part $w_1$ (beyond the anchoring means) may be chosen so as to be sufficiently great in order not to allow a spontaneous capillary flow SCF in the upper part. Thus the broadening from the lower part towards the upper part may preferably be by at least a factor of 2, preferably by at least a factor of 3.

The broadening from the lower part of the channel towards the upper part of the channel may depend on the angle formed by the anchoring ridge with the internal wall of the device in the case of non-broadening. Thus, in the case of non-broadening (anchoring ridge not present), this angle is zero. In the case of broadening, the anchoring ridge may form an angle greater than 20°, preferably greater than 50°, or even 60°, or even preferably between 80° and 100°. In other words, the angle formed by the anchoring ridge corresponds to the angle formed by the internal wall on either side of the anchoring ridge.

The anchoring means may also comprise a coating made locally hydrophobic. This coating may be placed at the interface between the lower part and the upper part. In this case, the broadening of the channel from the lower part towards the upper part may not be necessary. In other words, the width of the upper part may not be greater than that of the lower part. The lower and upper parts may for example have the same width. Nevertheless, it is preferable to have a broadening of the channel from the lower part towards the upper part and therefore for the upper part to have a width greater than that of the lower part.

Thus the presence of the blocking and anchoring means as described above makes it possible to confine the liquid respectively in a longitudinal direction (that is to say from the first end towards the second end) and in a transverse direction (that is to say from the lower part towards the upper part). Any risk of contact between the liquid and the outside of the channel at the upper surface of the channel, that is to say the surface joining the ends of the opposite internal walls at the channel bottom, is then prevented. Thus only the first end of the channel can be in contact with the external environment.

In this way, when the device is inserted in an analysis means, the latter is not contaminated by the liquid contained in the channel, unlike the solutions of the prior art presented above.

Moreover, the internal walls may be secant, in particular at the lower part of the channel, so as to form the channel bottom at their intersection. The capillary flow of the liquid is thus facilitated. In this case, the channel bottom corresponds to the intersection between the two internal walls.

Preferably, the two internal walls form at their intersection an acute angle of less than 40°. The acute angle thus formed may allow a spontaneous capillary flow SCF by "point effect".

According to a variant embodiment, the internal walls approach each other without being secant. In this case, the channel bottom corresponds to the surface joining the two internal walls in the lower part, when separation between the latter is minimal. This surface may be represented by a wall, referred to as a bottom wall.

The device according to the invention may also be functionalised by a reagent, in particular chemical or biological, intended to react with the liquid sample.

In particular, the channel may comprise, on at least one part thereof, at least one reagent, in particular chemical or biological, in dry and/or lyophilised form.

The reagent may in particular be situated upstream of an analysis zone of the channel, considering the flow of liquid from the first end towards the second end of the channel. In this way, the liquid may mix with the reagent during the flow before reaching the analysis zone of the channel.

The reagent may be deposited against at least one internal wall of the lower part of the channel, by a drying or lyophilisation method. When the reagent is deposited by drying, the deposition is on the surface. When the reagent is deposited by lyophilisation, the deposition is in the volume.

In order to achieve such a deposition, the reagent may be introduced into the channel in the liquid phase. The liquid solvent used is generally water. Drying generally takes place at ambient temperature and at atmospheric pressure or under vacuum by evaporation of the liquid phase, whereas the lyophilisation generally takes place at lower pressure or at low temperature by sublimation of the solid phase. In the latter case, the liquid phase, comprising the reagent, solidifies under the effect of the low temperature, generally below 10° C. The solid reagent is then subjected to low pressures promoting change from the solid state to the gaseous state. The solid phase sublimates. In the case of lyophilisation, the reagent in lyophilised form is present in the volume of the fluid channel in the form of a porous structure able to dissolve quickly in the presence of water. This porous structure itself being thirsty for water, it contributes to the pumping force of the liquid, and therefore contributes to its flow in the lower part of the channel.

Having an upper surface of the channel, that is to say the surface joining the ends of the internal walls opposite to the channel bottom, that is open promotes the drying or lyophilisation by optimising the surface area for evaporation or sublimation of the water. On the other hand, a channel that had a closed upper surface and openings only at its ends would require a much longer time for achieving evaporation or sublimation of the water.

It is desirable for the device to assist the most homogeneous possible deposition of the reagent on the internal wall or walls of the device.

For this purpose, the height of the channel, and in particular the height $h_1$ of the lower part of the channel, separating the channel bottom from the upper part of the channel, is advantageously is as small as possible. In addition, the height of the channel, and in particular the height $h_1$ of the lower part of the channel, advantageously remains substantially constant in extending along the channel bottom from the first end towards the second end.

The height $h_1$ of the lower part of the channel can in particular be less than or equal to 5 mm, preferably less than 2 mm, or even 1 mm, for example 0.7 mm.

The height $h_1$ of the lower part may for example be between 500 μm and 3 mm.

Having a height of the channel, and in particular a height of the lower part of the channel, that remains substantially constant makes it possible to maintain constant geometric conditions of evaporation and sublimation of the liquid solvent according to the advancement in the channel, that is to say according to the distance between a point on the channel and the first end of the channel. Thus the quantity per surface area of the reagent deposited (mass per surface area in the case of drying and mass per unit volume in the case of lyophilisation) can be identical whatever the advancement in the channel. This makes it possible to control the concentration of reagent, per surface or volume element, between the first end of the channel and the point of advancement in the channel. On the other hand, in the solutions of the prior art disclosed previously, the height of the channel does not remain constant and fluctuates with significant zones of increase in height.

Moreover, having a height of the channel, and in particular a height of the lower part of the channel, that is as small as possible may also assist the homogeneous presence of the reagent, since this minimises the difference in distance between the channel bottom and the upper part of the channel, intended to remain in contact with the ambient air. A small height $h_1$, as previously defined, facilitates the discharge of the solvent. In addition, this makes it possible to minimise the quantity of liquid sample introduced into the channel.

It is also desirable to be able to avoid, or at least to be able to limit, the formation of air bubbles when the liquid sample is taken with the device according to the invention.

To this end, the channel may extend in a substantially rectilinear direction from the first end towards the second end.

In a variant, the channel bottom may extend in a substantially concave direction from the first end towards the second end.

Moreover, it is also desirable to facilitate and optimise the collection of liquid sample with the device according to the invention.

The opening of the channel towards the outside of the device for collecting the liquid sample, at the first end, may thus have a substantially rounded shape, so as in particular to bring the channel bottom and the opening close together.

The device may comprise, at the first end of the channel, a contact surface for taking the liquid sample extending in a plane substantially perpendicular to at least one internal wall of the device.

The contact surface is advantageously intended to be placed close to the element from which it is wished to take a liquid sample. In particular, this element may be part of a body, for example a finger end, a lip or any other member from which it is wished to take a bodily fluid. The contact surface may thus be configured so as to enable it to be placed on such a part of the body. The contact surface may conform to such a part.

The contact surface may comprise a flow opening designed to emerge in the channel, for example in the upper part or the lower part of the channel, for example at the channel bottom. Thus, at the first end of the channel, the sample liquid may flow directly from the contact surface towards the channel by means of this flow opening. This flow opening may have a form identical to the cross section of the channel.

The contact surface may be splayed, being in particular convex towards the first end of the channel, to enable the liquid sample taken to go towards the flow opening and thus towards the channel. It may also be structured so as to assist the flow of liquid towards the flow opening, for example by means of microfurrows converging towards said opening.

The presence of such a contact surface may increase the collection efficiency and also prevent sample liquid flowing outside the device, in particular on its external surface. Only the channel and the contact surface are then liable to be in contact with the sampled liquid. Moreover, the contact surface may act as a support surface against which the element, in particular a body element, may be applied with a certain pressure. The pressure exerted on the element may facilitate the ejection of bodily fluid issuing from the body element.

Preferably, the contact surface is configured so that the central part of the body element does not come into direct contact with the element from which it is wished to take a sample of liquid. Only the liquid on the surface of the element comes into contact with the flow opening. The central part of the contact surface may at least partly comprise the flow opening designed to emerge in the channel, which may in particular be placed on the face of an incision, for example a prick, made on a body element through which the liquid to be sampled flows. Thus the pressure on the element is exerted only at the periphery of the incision, rather than on the incision itself. It is thus possible to obtain a good discharge of liquid, while enabling a pressure to be applied to the element concerned.

The contact surface may itself be structured so as to assist the emergence of the bodily fluid issuing from the body element. It may then comprise a support surface against which the body element is intended to bear for taking the liquid sample. Such a support surface may be annular, and preferably centred with respect to the flow opening. It may for example be a torus with a thickness of a few millimetres, for example between 1 and 5 mm, with a diameter of between 5 mm and 1.5 cm, and centred on the flow opening. When the body element is a finger that has been incised, the bearing of the finger against the support surface assists the flow of blood towards said incision. The support surface, preferably annular, may be circular or elliptical, in order to conform to the body element from which the bodily fluid is extracted.

The upper surface of the channel, that is to say the surface joining the ends of the internal walls opposite to the channel bottom, is preferably open, giving onto the outside. Whatever the case, it is preferable for the upper surface of the channel to comprise an opening, preferably close to the second end, this opening acting as a vent for driving out the air initially contained in the channel.

The presence of an opening on the upper surface of the channel, in particular when the upper surface of the channel is completely open, makes it possible to more easily carry out chemical treatment of the inside of the channel, in particular of the interior surface of the channel. For example, a surface chemical treatment, in particular by plasma, for example $O_2$ plasma, may make it possible to reduce the wetting angle of the liquid sample with respect to an internal wall of the device.

Moreover, the internal walls of the device may be produced from a material that is transparent or translucent, in particular to the visible or near infrared range. In this way it may be possible to carry out an optical analysis of the liquid contained in the channel. An optical measurement may in particular be carried out along an optical axis substantially perpendicular to the internal walls delimiting the channel.

To allow a correct optical measurement, around the analysis zone of the channel in particular, the internal walls preferably have good quality with respect to surface evenness and low roughness to allow good transmission of optical rays. Thus, preferably, the internal walls are substantially parallel to each other, in particular the lower part of the channel. This makes it possible to illuminate the liquid contained in the channel by means of an optical beam substantially perpendicular to the two internal walls. In other words, this makes it possible to define a direction normal to the two internal walls along which a light beam can be arranged along with the optical axis of an analysis means, in particular a photodetector.

The device, and in particular the internal walls, may for example be produced by moulding or injecting a plastics material such as polycarbonate, polypropylene, polyethylene, cyclic olefin copolymer (COC) or cyclic olefin polymer (COP), among others.

The device may also comprise a piercing means, in particular a needle, for piercing the skin of a patient in order to collect the liquid sample. This piercing means may preferably be situated close to the first end of the channel.

This piercing means may be movable in the device in order to perform the step of incision of piercing in the skin when the body element is placed in abutment on the support surface. The piercing means able to move in the device can be deployed, so as to be applied quickly against the body element, in order to form an incision in the latter. Then it can be retracted in the device. Thus the piercing means can be deployed from a retracted position to a deployed position so as to make the incision and then be retracted into said retracted position. Elastic return means can allow the movement of the piercing means.

In the case of a fixed piercing means, for example a fixed needle, the device provided with such a piercing means may first of all be used in a projection instrument enabling the piercing means to strike the skin of the patient with a projection speed and a piercing-depth travel that are necessary for making a sufficient incision to make a drop of liquid sample emerge, for example blood, on the surface of the skin, and then to withdraw the piercing means at a controlled speed. Then the device can be used to take the sample of liquid thus obtained, by means of the first end of the channel.

The device may comprise at least two channels for sampling the same liquid or at least two separate liquids. This makes it possible for example to compare measurements made in each channel. The first ends of said at least two channels may be situated close to each other to allow in particular simultaneous contact with the liquid sample or samples to be taken, for example a drop of blood. Each channel of such a device may, where applicable, be filled with a specific reagent, on each different occasion, to carry out for example multiparametric diagnostic tests.

The height of the channel of the device may be variable, increasing over at least a first portion of the channel.

In particular, according to one embodiment of the invention, the channel may comprise a concave part, extending over a first portion lying between a first distance and a second distance with respect to the first end of the channel. Advantageously, this concave part may allow an increase in the depth of the channel.

Preferably, the first portion is situated close to the first end. Such a configuration may allow a draining of the liquid towards the channel bottom. It also allows a fluid flow limiting the risk of appearance of air bubbles in the channel.

Another subject matter of the invention, according to another of its aspects, is a method for analysing a liquid sample taken by means of a device as defined above, in which the device is subjected to analysis means, able to analyse the liquid contained in the channel at at least one predetermined analysis zone of the channel.

The analysis zone may be situated at any level in the channel. For example, the analysis zone may be situated at the centre of the channel.

The device may for example be introduced into an optical analysis means so as to permit an analysis of the liquid contained in the analysis zone of the channel. The analysis zone may be illuminated by a light beam, and an optical sensor may generate an image of the analysed zone. Treatment of this image may give information on at least one parameter of the liquid analysed.

The method according to the invention may comprise any one of the previously stated features, taken in isolation or according to all technically possible combinations with other features.

Another subject matter of the invention, according to another of its aspects, is the use of a device as defined previously, for taking a liquid sample by capillarity, in particular a drop of blood.

The device for taking the liquid sample may be used when at least one reagent is already present in the device, in particular on at least one of the internal walls with respect to a dried reagent or in the volume of the internal walls in respect of a lyophilised reagent.

In addition, before its use for taking the liquid sample, the device may already be present in analysis means, in particular optical or electrical analysis means.

The liquid sample, in particular the drop of blood, may already be present on the body element, in particular a finger end, before use of the device. Thus the device may for example be used by placing it in abutment on the body element, for example using a support surface of the device, to enable the liquid sample to be taken.

In a variant, the liquid sample, in particular the drop of blood, is not present on the body element, in particular the finger end, before use of the device. The analysis means may then comprise a piercing means, in particular a needle, to enable the skin to be pierced in order to collect the liquid sample.

BRIEF DESCRIPTION OF THE DRAWINGS

The invention can be better understood from a reading of the following detailed description of non-limitative example embodiments thereof, and from an examination of the schematic partial figures in the accompanying drawing, in which:

FIG. 1A depicts a first example of a sampling device according to the invention, FIG. 1B shows a cross section along B-B of the device of FIG. 1A, FIG. 1C is a front view along C of the device of FIG. 1A, FIGS. 2A, 2B and 2C illustrate the steps of filling the sampling device of FIG. 1A with liquid, FIG. 17A shows another example embodiment of a sampling device according to the invention, with a variable channel height, FIG. 17B is a partial view in cross section along B-B of the device of FIG. 17A, and FIGS. 18A to 18D show a modelling of the flow of a liquid over time, respectively during four steps, in the channel of the device of FIG. 17A.

In all these figures, identical references may designate identical or similar elements.

Figure 2C:
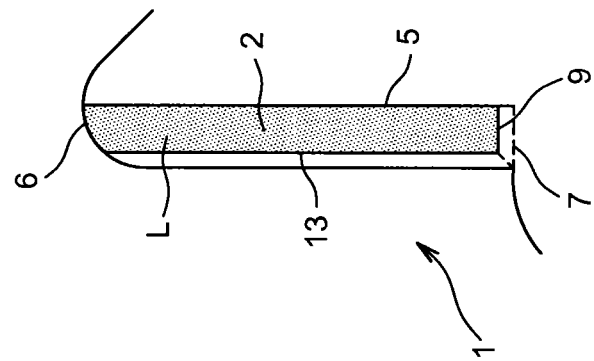

In addition, the various parts depicted in the figures are not necessarily shown according to a uniform scale, in order to make the figures more legible.

DETAILED DISCLOSURE OF PARTICULAR EMBODIMENTS

FIGS. 1A, 1B and 1C show a first example of a device 1 for taking a liquid sample L by capillarity according to the invention.

FIG. 1A is a profile view of the device 1, FIG. 1B is a view in cross-section along B-B in FIG. 1A and FIG. 1C is a front view along C of the device 1 of FIG. 1A.

In accordance with the invention, the device 1 comprises a channel 2 for flow of the liquid L delimited by two internal walls 3 and 4, or lateral walls, between which a channel bottom 5 extends. The distance D, visible in FIG. 1C, between the two internal walls 3 and 4 decreases in the direction of the channel bottom 5. In addition, the channel bottom 2 extends from a first collecting end 6, open to the outside E of the device 1 and able to receive the liquid L, and a second end 7, so as to enable the liquid L to flow by capillarity along the channel bottom 5 from the first end 6 to the second end 7.

Thus the overall form of the channel 2, defined by the internal walls 3 and 4, thins from the upper surface 18 of the channel 2, that is to say the surface joining the ends of the internal walls 3 and 4 opposite to the channel bottom 5, towards the channel bottom 5, the upper surface 18 of the channel 2 being open to the outside E. The form of the channel 2 thinning from this upper surface 18 towards the channel bottom 5 makes it possible to obtain a capillarity force of the channel 2 that is greater at the channel bottom 5 than at the upper surface 18 open to the outside E.

Moreover, in order to control the filling of the channel 2 with liquid L and to prevent any contamination of the outside E by the liquid L, one or more means for blocking the flow of liquid L along the channel bottom 5 can be provided. These means make it possible to block the flow of liquid at the second end or upstream of the latter.

Such a blocking means may for example be in the form of a wall 17 for closing the channel 2, situated in particular at the second end 7 of the channel 2. Such a closure wall 17 can extend transversely between the internal walls 3 and 4 to close the channel 2, in particular at the second end 7.

Such a blocking means may also be in the form of a coating made locally hydrophobic (not shown) in order to prevent the flow of liquid L. This coating may be situated in particular at the second end 7 of the channel 2 and for example at the channel bottom 5 and/or at one or more of the two internal walls 3 and 4.

In the example shown in FIGS. 1A, 1B and 1C, the channel 2 comprises two blocking means, one on each internal wall 3, 4, in the form of two blocking ridges 9 that afford a broadening of a part of the channel 2, in particular a broadening of the second end 7 of the channel 2. The two blocking ridges 9 are in particular visible in FIGS. 1A and 1C.

The blocking ridges 9 may make it possible to stop the capillary filling of the liquid L in the channel 2 and may thus make it possible to perfectly control the volume of liquid sample L taken by the device 1.

A blocking means may also comprise a gradual broadening of the channel bottom 5, upstream of the second end 7. Such a broadening reduces the capillarity force applied to the liquid, which constitutes the engine for the flow. The result is a reduction in the rate of progress of the liquid along the channel bottom 5. When the channel bottom 5 is a line, formed by the intersection of the lateral walls 3 and 4, at the broadening, the channel bottom 5 takes the form of a flat surface, the width of which increases gradually from a negligible value (the width of a line) to 50 µm, or even between 150 and 200 µm.

The blocking means described above may be combined. In particular, the device may comprise a first blocking means disposed upstream of a closure wall of the channel. Such a combination slows down the flow of liquid upstream of said closure wall.

The device 1 may comprise a zone for filling of the liquid sample L situated at the first end 6 of the channel 2 and a zone for stopping the liquid L situated at the second end 7 of the channel 2.

An analysis zone 15, in particular an optical measurement zone, can be provided over the extent of the channel 2, in particular in a central part of the channel 2, as can be seen in FIG. 1A. This analysis zone 15 may make it possible to determine one or more parameters of the liquid sample L by a suitable analysis means thereat, in particular an optical analysis means able to direct an optical beam onto this analysis zone 15. Preferably, the internal walls 3 and 4 may thus be at least partially transparent or translucent, in particular at the analysis zone 15 of the channel 2.

Moreover, as can be seen more easily in FIG. 1C, the channel 2 is divided into a lower part 11 comprising the channel bottom 5 and an upper part 12 so that the lower part 11 is situated between the channel bottom 5 and the upper part 12. The lower 11 and upper parts 12 are delimited by the internal walls 3 and 4, the lower part 11 having a capillary force greater than that of the upper part 12 so as to allow a spontaneous capillary flow SCF of the liquid L along the channel bottom 5 from the first end 6 to the second end 7.

Separation between the lower 11 and upper 12 parts of the channel 2 can be achieved by means 13 for anchoring the liquid L on at least one internal wall 3, 4 of the device 1, affording a blocking of the flow of liquid L from the lower part 11 towards the upper part 12.

More particularly, as can be seen in particular in FIG. 1B, the channel 2 may comprise two anchoring means situated respectively on each internal wall 3, 4, these anchoring means being in the form of anchoring ridges 13. Preferably, these anchoring means extend from the first end 6 towards the second end 7, parallel to the channel bottom 5. This constitutes a lower part 11 the depth of which is constant from the first end 6 towards the second end 7.

The anchoring ridges 13 can thus prevent a flow of the liquid L towards the outside E of the device 1, beyond the lower part 11 of the channel 2.

In other words, by virtue of the anchoring ridges 13 and the blocking ridges 9, it is possible to maintain a confinement of the liquid L in the lower part 11 of the channel 2, as shown schematically by the zone in broken lines in FIG. 1A.

The broadening of the channel 2 obtained by means of the blocking ridges 9 may depend on the angle $\Omega$ formed by a blocking ridge 9 with an internal wall 3 or 4 of the device 1 in the case of non-broadening. More specifically, in the case of non-broadening (a blocking ridge 9 not present), this angle $\Omega$ is zero. In the case of broadening, as can be seen in FIG. 1B, the blocking ridge 9 may for example form an angle $\Omega$ greater than 20°.

Moreover, the broadening obtained by the presence of anchoring ridges 13 from the lower part 11 of the channel 2 towards the upper part 12 of the channel 2 may depend on the angle formed by an anchoring ridge 13 with an internal wall 3 or 4 of the device 1 in the case of non-broadening. More specifically, in the case of non-broadening (anchoring ridge 13 not present), this angle is zero. In the case of broadening, the anchoring ridge 13 may form an angle Ω greater than 20°, being in particular equal to 90° in the example shown in FIG. 1C.

Figure 2B:
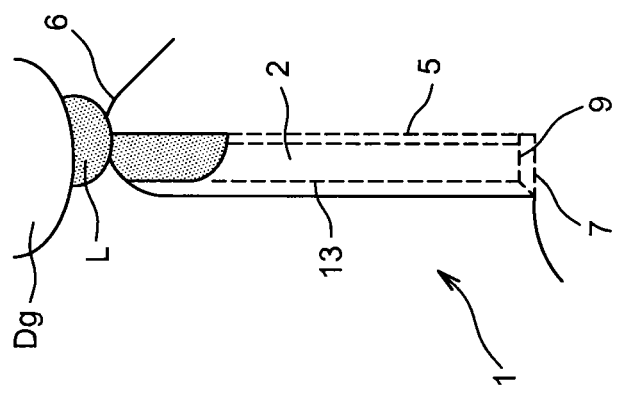
Figure 2A:
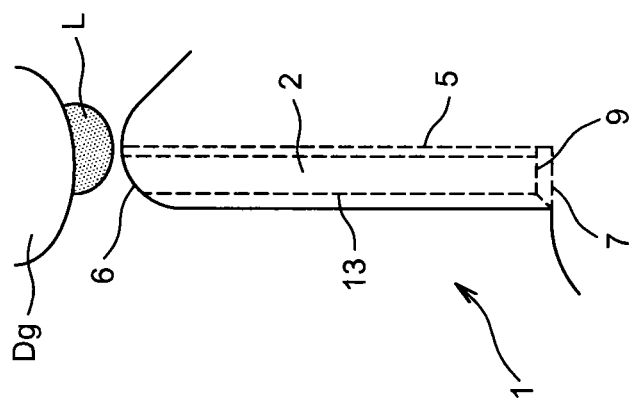

FIGS. 2A, 2B and 2C show the steps of the taking of a liquid sample L by the sampling device 1 in FIGS. 1A, 1B and 1C.

The device 1 may for example be used for sampling a drop of blood L formed at the end of a finger $D_g$ of a user, intended to be analysed.

To allow the correct filling of the device 1 with the liquid L, the device 1 is placed in contact with the drop of blood by means of the first collecting end 6 of the channel 2, as can be seen in FIG. 2A.

Then, as can be seen in FIG. 2B, the channel 2 fills with liquid L by capillarity, the liquid L extending along the channel bottom 5 from the first end 6 in the direction of the second end 7.

Then, as can be seen in FIG. 2C, the liquid L fills the channel 2 completely while being confined inside the lower part 11 of the channel 2 by blocking of the liquid L by means of the blocking ridges 9 and the anchoring ridges 13.

Figure 3A:
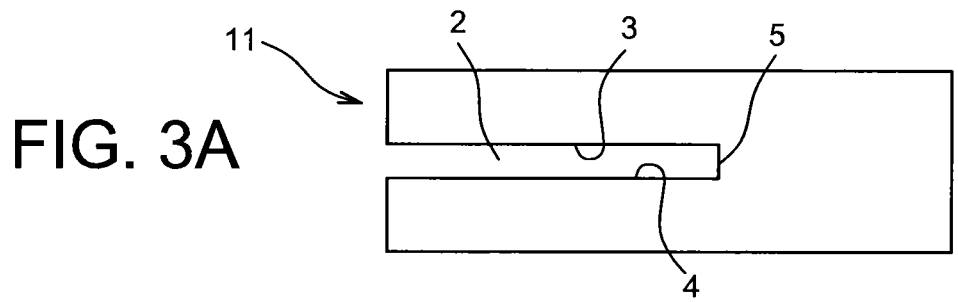
FIGS. 3A and 3B illustrate two example embodiments of the lower part of the channel of a device according to the invention.
Figure 3B:
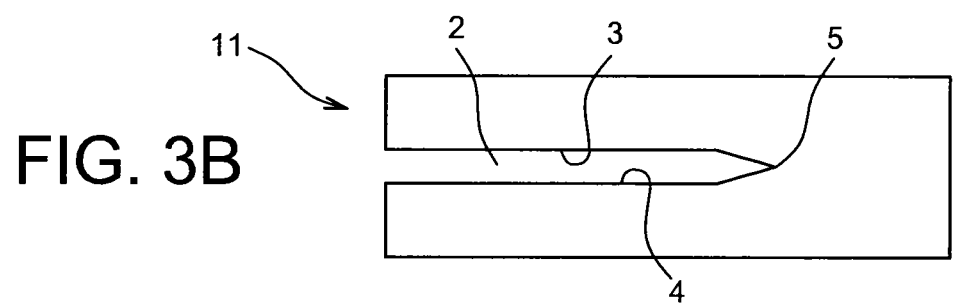

FIGS. 3A and 3B show two example embodiments of the lower part 11 of the channel 2. In the example in FIG. 3A, the channel bottom 5 consists of a wall perpendicular to the internal walls 3 and 4 of the device 1, whereas in the example in FIG. 3B the internal walls 3 and 4 are secant so as to form the channel bottom 5 at their intersection.

Preferably, the channel bottom 5 is formed by the intersection of secant internal walls 3 and 4 as shown in FIG. 3B.

Figure 4A:
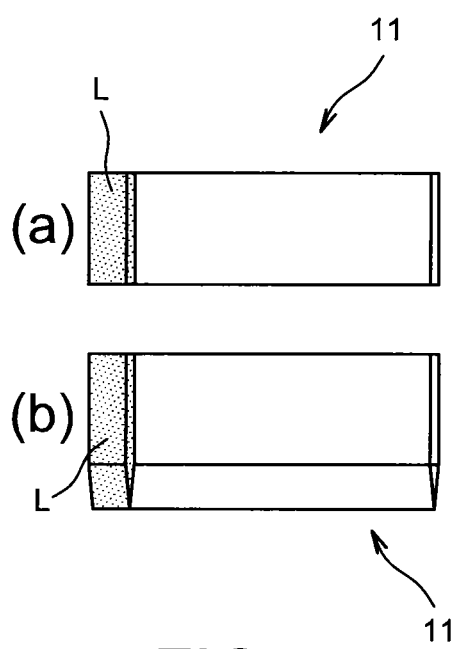
FIGS. 4A and 4B show the modelling of the liquid flow over time with comparison between the behaviours of the lower parts of FIGS. 3A and 3B.
Figure 4B:
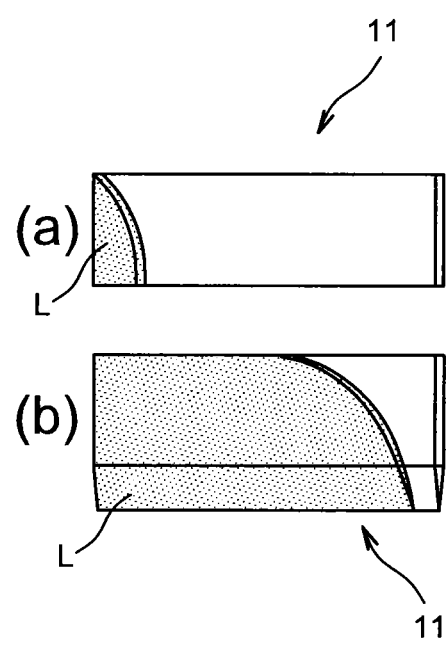

FIGS. 4A and 4B illustrate simulation results concerning the speed of filling of the lower parts 11 of the channel 2. These simulations were made by a finite elements method taking account of the capillarity forces for a wetting angle θ between the liquid L and a lower internal wall at 78°.

FIG. 4A shows a lower part 11 of the channel 2 of the type in FIG. 3A (for case a) and a lower part 11 of the channel 2 of the type in FIG. 3B (for case b) at an initial time. FIG. 4B shows the comparison between the same lower parts 11 of the channel 2 at a filling time t.

Thus, when the two lower parts 11 are put in contact at the same initial time (FIG. 4A) and when the filling of these two lower parts 11 with liquid L at a given time t is observed (FIG. 4B), it is noted that the lower part 11 having a bottom 5 of the channel 2 formed by the intersection of secant internal walls 3 and 4 (case b) fills much more quickly than the lower part 11 of the channel 2 having a channel bottom 5 formed by a wall perpendicular to the internal walls 3 and 4 (case a). In addition, the greater capillarity force of the conically shaped channel bottom 5 (case b) makes it possible to create a faster filling while limiting the formation of air bubbles.

Figure 5A:
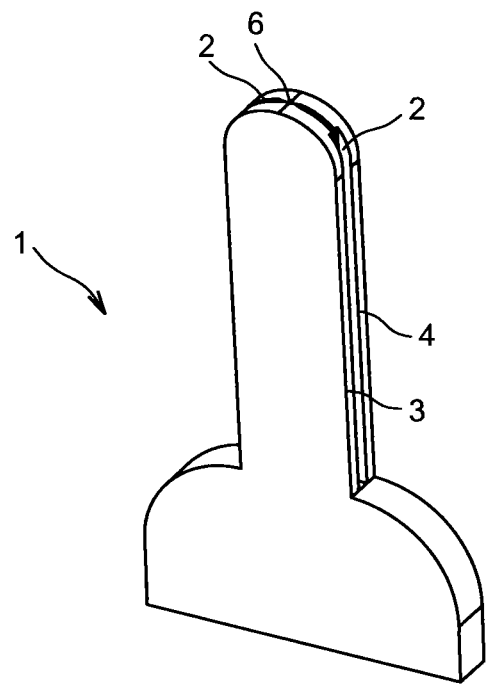
FIG. 5A shows in perspective a second example embodiment of a sampling device according to the invention.
Figure 5B:
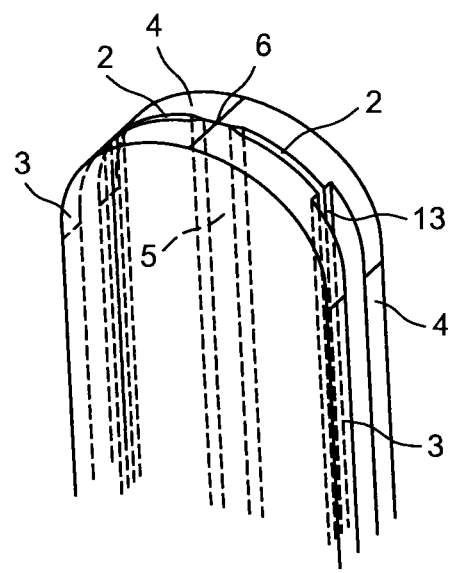
FIG. 5B is an enlarged view of the sampling device of FIG. 5A, FIGS. 6A and 6B show in perspective a third example embodiment of a sampling device according to the invention.

FIGS. 5A and 5B show a second example embodiment of a device 1 for taking a liquid sample L by capillarity in accordance with the invention. FIG. 5A shows such a device 1 in perspective and FIG. 5B is an enlarged view of this device 1.

In this example, the channel 2 is produced in a similar fashion to the one in the example in FIGS. 1A, 1B and 1C. However, in the upper part 12 of the channel 2, the internal walls 3 and 4 are parallel to each other whereas in the example in FIGS. 1A, 1B and 1C the internal walls 3 and 4 are oriented obliquely in the direction of the channel bottom 5.

The device 1 in FIGS. 5A and 5B advantageously comprises two channels 2 disposed so as to be juxtaposed with each other, so that the two channels 2 have the same first end 6 intended to come into contact with the liquid sample L during sampling.

In general terms, the device 1 may comprise a reagent in the channel 2, in particular in dry or lyophilised form, intended to react with the liquid sample L, this reagent being in particular situated upstream of the second end 7 considering the flow of liquid L from the first end 6 towards the second end 7.

In the case of the device 1 in FIGS. 5A and 5B, each channel 2 may be filled with the same reagent or with reagents that are different from each other so as to be able to carry out multiparametric diagnostic tests.

Figure 6A:
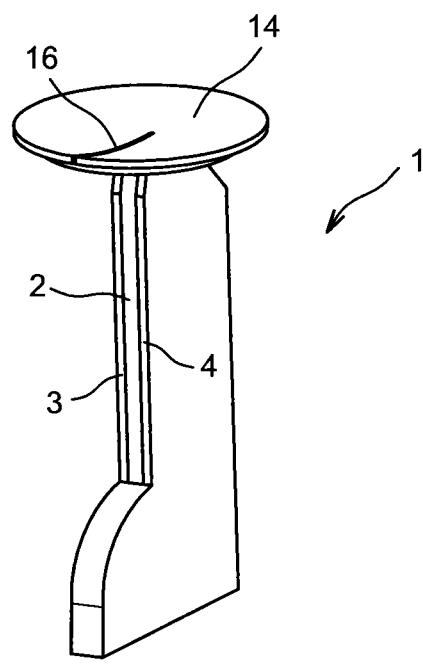
Figure 6B:
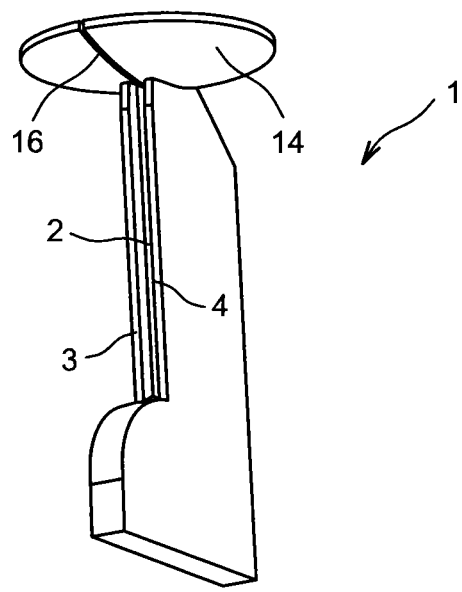

FIGS. 6A and 6B show a third example embodiment of a device 1 for taking a sample of liquid L by capillarity in accordance with the invention.

In this example, the device 1 is more or less similar to that described with reference to FIGS. 1A, 1B and 1C. However, the device 1 comprises, at the first end 6 of the channel 2, a contact surface 14 enabling the liquid sample L to be taken, this contact surface 14 extending in a plane substantially perpendicular to the internal walls 3 and 4 of the device 1.

The contact surface 14 further comprises a flow opening 16 designed to emerge in the channel 2.

The contact surface 14 is advantageously intended to be approached by, or even to come into contact with, an element from which it is wished to take a sample of liquid L, this element being in particular able to be a body element, for example a finger, a lip or any other member from which it is wished to sample a bodily fluid. In this way, the contact surface 14 may be configured so as to be able to be approached by such a body element, or even to come into contact with the body element. In particular, the contact surface 14 may be curved, being oriented so as to be concave with respect to the element from which it is wished to take the liquid sample L, as can be seen in FIGS. 6A and 6B. This makes it possible to guide the bodily fluid sampled towards the flow opening 16 of the channel 2.

The presence of such a contact surface 14 may make it possible to increase the collection efficiency and also prevent the sampled liquid L flowing to the outside E of the device 1.

Advantageously, the contact surface 14 is configured so that its central part does not come into contact with the element from which it is wished to take a liquid sample L. The flow opening 16 may be formed at least partly in the central part of the contact surface 14 so as to emerge at the lower part 11, in particular at the bottom 5 of the channel.

FIGS. 7 to 11 serve to illustrate considerations on the conditions for obtaining a spontaneous capillary flow SCF by capillarity in the device 1 and also make it possible to define dimensions of the device 1.

Figure 7:
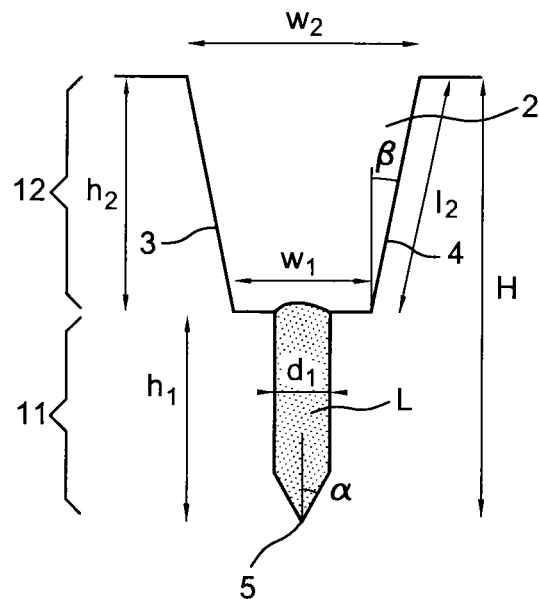
FIG. 7 shows an example embodiment of a channel of a device according to the invention.

FIG. 7 depicts partially a first example of a device 1 comprising a channel 2 divided into a lower part 11 and an upper part 12. The internal walls 3 and 4 are secant in order to form the channel bottom 5.

Thus the device 1 is overall in the form of a fine capillary V in the lower part 11 with a broadening in the upper part 12. The point formed by the channel bottom 5 forms a filament that progresses in an uninterrupted fashion by what is referred to as a Concus-Finn effect. The upper part 12 is sized so as to not fill with liquid L and can allow manipulation of the device 1.

The capillary flow is facilitated by having a V-shaped dihedron. The condition for obtaining a capillary flow is the Concus-Finn condition, which is stated as follows:

$$\theta < \frac{\pi}{2} - \alpha,$$

where θ is the angle of contact of the liquid L with the internal walls 3 and 4, also referred to as the wetting angle or Young angle, α is the half-angle of the dihedron, as shown in FIG. 7.

For example, if α is equal to 5°, then it is necessary for θ to be strictly less than 85°.

Figure 8:
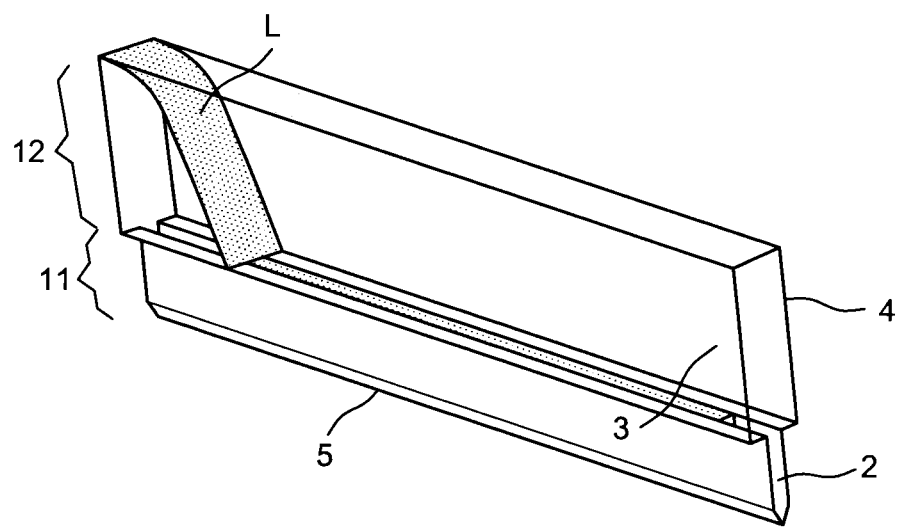
FIG. 8 illustrates the spontaneous capillary flow SCF by point effect in the channel of a device according to the invention.

The Concus-Finn effect makes it possible to obtain a "point effect" when the liquid L flows in the channel 2, as can be seen in FIG. 8.

The so-called Concus-Finn condition disclosed above can make it possible to size the lower part 11 of the channel 2 according to the contact angle θ.

However, it may be necessary in practice to take a few additional precautions to take account of surface imperfections, and thus to choose a slightly lower angle than the one obtained by the theoretical Concus-Finn formula.

It is also necessary to be able to size the upper part 12 of the channel 2 so as to obtain a spontaneous capillary flow SCF that allows a flow by capillarity along the channel bottom 5 in the lower part 11, as shown in FIG. 8, but without invading the upper part 12 of the channel 2.

To do this, it is assumed that the width $d_1$ of the channel 2 in the lower part 11 and the half-angle α, as both shown in FIG. 8, are known.

Then a study carried out with the Evolver software showed that it is possible to avoid the invasion of the upper part 12 of the channel 2 by a suitable increase in the cross section of flow $w_1$ of the upper part 12 of the channel 2, as shown in FIG. 7.

The condition for obtaining a spontaneous capillary flow SCF, determined from the Gibbs thermodynamic equation, is then written:

$$w_2/(2l_2+(w_1-d_1)) < \cos \theta.$$

Then, after the geometric consideration according to which $h_2 = l_2 \times \cos \beta$, the condition in order not to have spontaneous capillary flow SCF in the upper part 12 of the channel 2 is as follows:

$$h_2 < [w_1 \cos \beta(1-\cos \theta)+d_1 \cos \beta \cos \theta]/[2(1-\sin \beta)].$$

Figure 9:
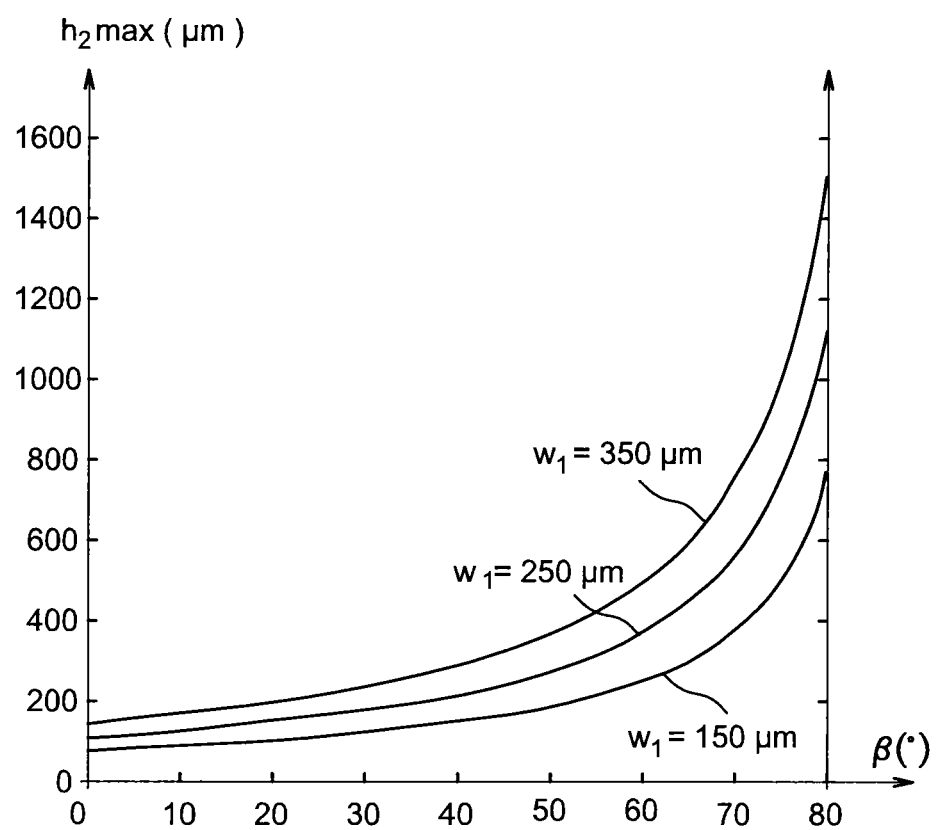
FIG. 9 is a graph showing the change in the maximum height $h_{2max}$ of the upper part of the channel in FIG. 7 as a function of the angle of inclination β of the internal walls in the upper part, for three different values of the width $w_1$ of the upper part.

FIG. 9 illustrates the relationship disclosed above for the case where $d_1$ is equal to 100 μm and θ is equal to 70°, for three values of $w_1$ equal to 150, 250 and 350 μm. More particularly, the three curves shown in FIG. 9 represent the maximum height $h_{2max}$ of the upper part 12 of the channel 2 as a function of the angle of inclination β.

Thus, for example, in the case of an angle β chosen so as to be equal to approximately 10°, as in the example in FIG. 7, there is an advantage in increasing $w_1$ so as to obtain a height $h_2$ that is not too small. For example, it is possible to have $h_2$ equal to approximately 170 μm with $w_1$ chosen equal to approximately 350 μm.

Figure 10:
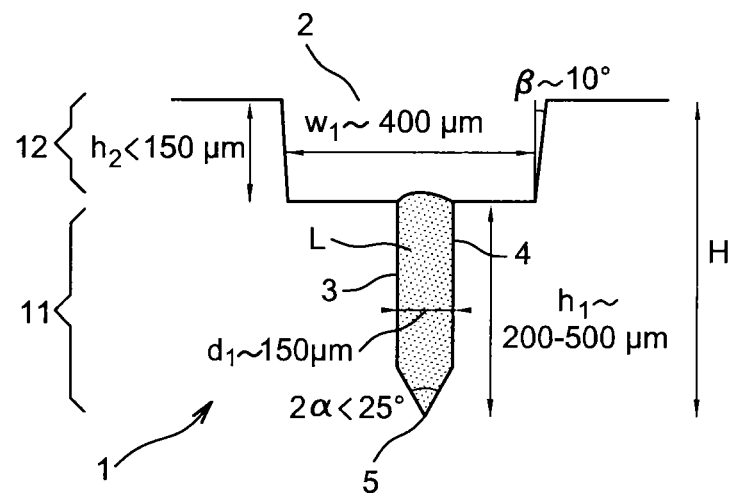
FIGS. 10 and 11 show other example embodiments for a channel of a device according to the invention.
Figure 11:
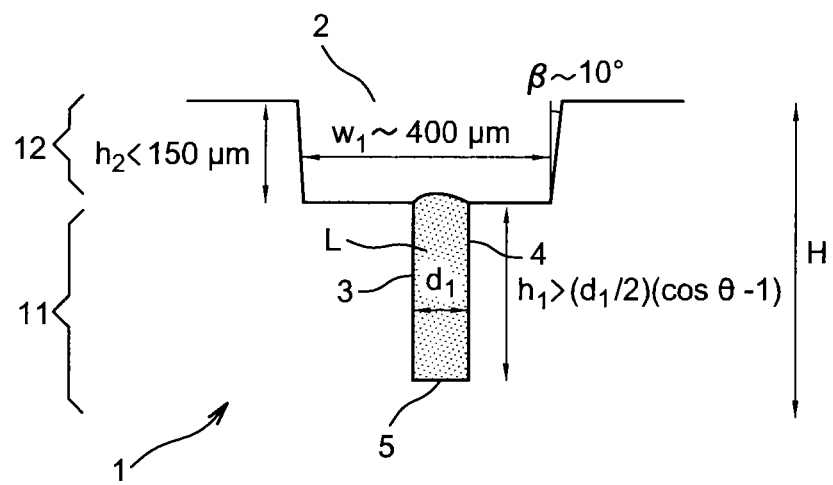

FIGS. 10 and 11 show two examples of channels 2 of a device 1, which differ in that, in the example in FIG. 10, the channel bottom 5 is formed by the intersection of the internal walls 3 and 4 forming a point, whereas in the example in FIG. 11 the channel bottom 5 is a wall extending perpendicularly between the internal walls 3 and 4.

For example, in the case in FIG. 10, a satisfactory sizing of the lower 11 and upper 12 parts of the channel 2 consists of having a fairly fine point at the channel bottom 5. The height $h_1$ of the lower part 11 may for example be around 200 to 500 μm and the width $d_1$ may for example be around 150 μm with a point angle 2α for example less than 25°.

The height $h_2$ of the upper part 12 may for example be less than 150 μm, the width $w_1$ may for example be around 400 μm and the angle β may be around 10°.

In order to have a spontaneous capillary flow SCF in the upper part 12, there is for example an advantage in having an abrupt broadening with a value $w_1$ equal to approximately 400 μm and a height $h_2$ strictly less than 150 μm.

In the example in FIG. 11, the device 1 does not use the Concus-Finn effect but only the spontaneous capillary flow SCF condition. This is then written as follows:

$$d_1/(2h_2+d_1) < \cos \theta$$

Thus, in order to obtain a spontaneous capillary flow SCF, it is necessary for the ratio between the height $h_2$ of the lower part 11 of the channel 2 and the width $d_1$ to satisfy the following condition:

$$(h_2/d_1) > \frac{1}{2}[(1/\cos\theta) - 1]$$

For example, for $d_1$ equal to 150 μm and θ equal to 85°, $h_1$ is strictly greater than 785 μm.

Moreover, when a deposit of reagent, for example in dried or lyophilised form, is provided in the channel 2, this reagent being intended to react with the liquid sample L, it is desirable for the deposition of the reagent to take place as homogeneously as possible.

Under these circumstances, the height H of the channel 2, and in particular the height $h_1$ of the lower part 11 of the channel 2, is designed to remain substantially constant extending along the channel bottom 5 from the first end 6 towards the second end 7 of the channel 2.

In addition, as well as being constant along the bottom 5 of the channel, the height $h_1$ of the lower part 11 of the channel 2 must preferably be less than or equal to 5 mm, better 2 mm, or even 1 mm, or even again 0.7 mm.

Furthermore, it is also desirable for the device 1 to be able to be filled with the liquid sample L without generating an excessively great formation of air bubbles.

FIGS. 12A, 12B, 12C and 12D illustrate the change in the interface I (curved lines in the lower 11 and upper 12 parts of the channel 2 in FIGS. 12A to 12D) between the liquid L and the air when the device 1 is filled with the liquid sample L, and this for various configurations of the channel 2, in particular for various forms of the generatrix of the channel 2 along the channel bottom 5.

Figure 12A:
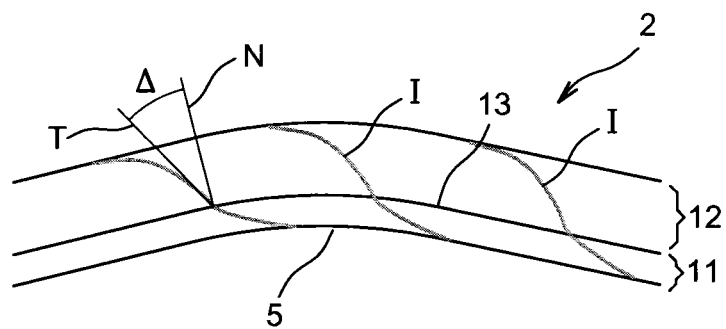
FIGS. 12A, 12B, 12C and 12D illustrate possibilities for orientation of the direction along which a channel of a device according to the invention extends.
Figure 12B:
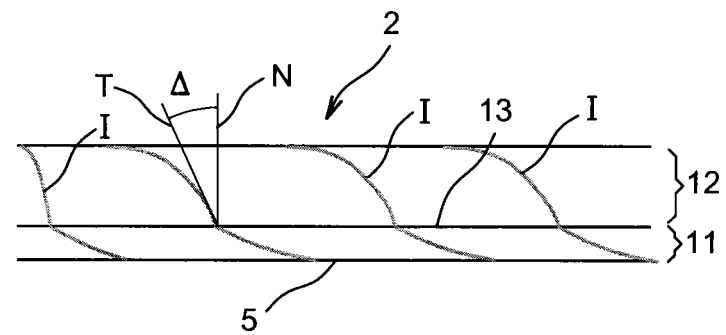
Figure 12C:
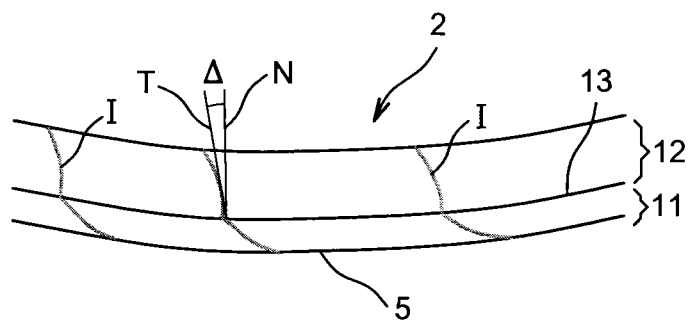
Figure 12D:
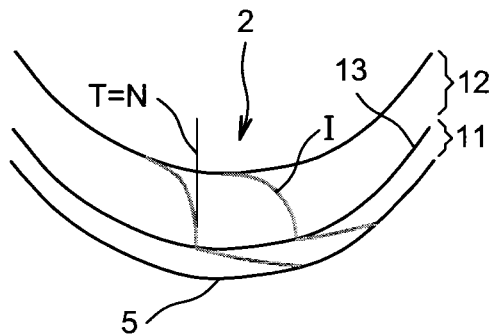

Thus FIG. 12A shows a channel 2 extending in a concave direction so that a segment joining two points on the channel is not necessarily included in this channel, FIG. 12B shows the channel 2 extending in a planar direction, and FIGS. 12C to 12D show channels 2 extending in a convex direction, with different concavities.

The changes in the interfaces I between the liquid and the air in FIGS. 12A to 12D were modelled using the Evolver software.

A comparison of FIGS. 12A to 12D shows that, at the anchoring ridge 13 marking the separation between the lower 11 and upper 12 zones of the channel 2, the tangent T to the interface I between the liquid and the air forms an angle Δ with the normal N to the anchoring ridge 13.

When the channel 2 extends in a convex direction (the case in FIGS. 12C and 12D), this angle Δ is small, or even zero for FIG. 12D. Thus the tangent T to the interface I between the liquid and the air approaches the normal N to the anchoring ridge 13, and even more so when the concavity of the channel 2 is pronounced.

Under these conditions, the risk of formation of an air bubble, in particular at the anchoring ridge 13, is great. This is because the tangent T to the interface I, and the anchoring ridge 13, may be merged with the normal N to the anchoring ridge 13, or even exceed it, depending on local heterogeneities, for example a fluctuation in the surface state. This configuration is propitious to a filling of the upper part 12 that is faster than the filling of the lower part 11 of the channel 2, and this may thus give rise to the trapping of an air bubble, in particular at the anchoring ridge 13.

Conversely, when the channel 2 extends in a rectilinear direction (the case in FIG. 12B) or concave direction (the case in FIG. 12A), the angle Δ is larger, which means that, at the anchoring ridge 13, the tangent T to the interface I forms a large angle, in particular strictly greater than 20°, with the normal N to the anchoring ridge 13. These conditions are appreciably less propitious to the formation of an air bubble, the filling speed of the upper part 12 of the channel 2 then being similar to the filling speed of the lower part 11 of the channel 2.

Figure 13A:
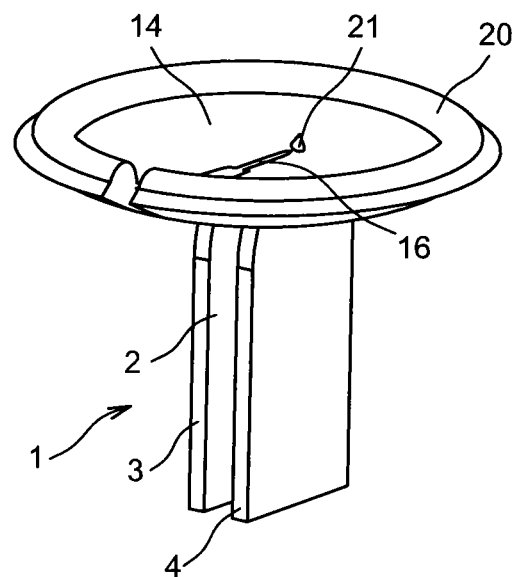
FIGS. 13A and 13B show another example embodiment of a device according to the invention comprising a support surface and a piercing means, respectively with the piercing means in the deployed position and in the retracted position.
Figure 13B:
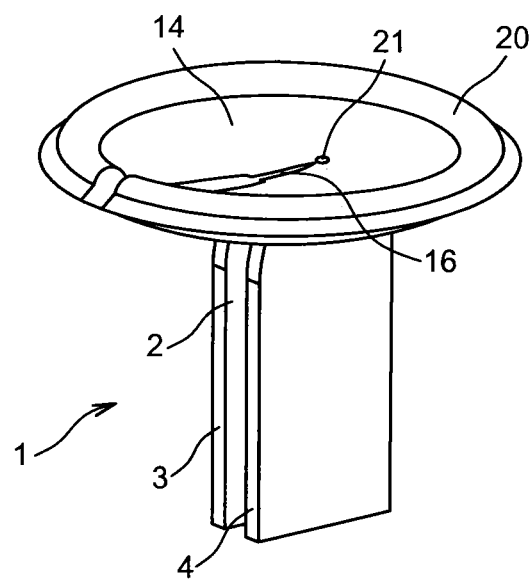

FIGS. 13A and 13B show another example embodiment of a device 1 for taking a sample of liquid L by capillarity according to the invention.

In this example, the device 1 comprises, as for the example embodiment in FIGS. 6A and 6B, at the first end 6 of the channel 2, a contact surface 14 enabling the liquid sample L to be taken, this contact surface 14 extending in a plane substantially perpendicular to the internal walls 3 and 4 of the device 1.

The contact surface 14 further comprises a flow opening 16 designed to emerge in the channel 2.

The contact surface 14 is itself structured so as to assist the emergence of the bodily fluid L issuing from the body element. Thus it comprises a support surface 20 against which the body element is intended to bear.

The support surface 20 is annular and centred with respect to the flow opening 16. In particular, the support surface 20 is, in this example, formed by a torus having a thickness between for example 1 and 5 mm and a diameter between for example 5 mm and 1.5 cm.

The support surface 16 in the form of a circular torus can make it possible to produce a protrusion that can serve as a support for the body element, for example a finger around the sampling zone of the finger, that is to say the zone where a drop of blood forms from the sampling, for example after action of a piercing means.

Moreover, the device 1 comprises a piercing means, in particular in the form of a needle 21, to enable the skin to be pierced in order to collect the liquid sample L. This needle 21 is preferentially situated close to the first end 6 of the channel 2.

The needle 21 may be able to move in the device 1 in order to perform the step of incision or piercing of the skin when the body element is placed in abutment on the support surface 20. Thus the needle 21 able to move in the device 1 can be deployed so as to be applied quickly against the body element, so as to form an incision in the latter. Then it can be retracted in the device 1. Thus the needle 21 can be deployed, from a retracted position as illustrated in FIG. 13B, to a deployed position as illustrated in FIG. 13A, so as to make the incision, and then be retracted into said retracted position.

Figure 14:
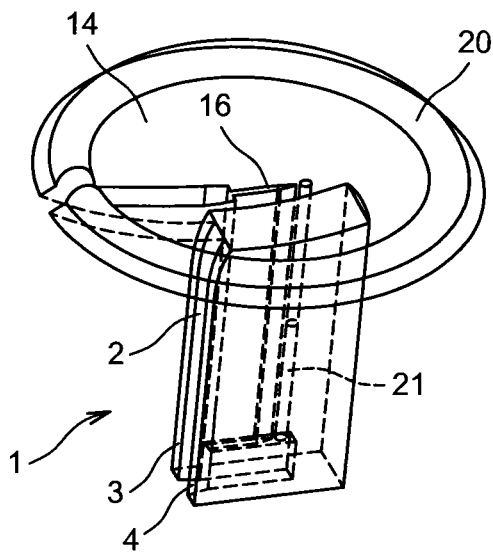
FIG. 14 shows the internal structure of the device of FIGS. 13A and 13B.

FIG. 14 shows the internal structure of the device 1 in FIGS. 13A and 13B.

Elastic return means may for example be provided inside the device 1 to enable the piercing means 21 to be moved from the retracted position (illustrated in FIG. 13B) to the deployed position (illustrated in FIG. 13A).

In a variant that is not illustrated, the needle 21 may be fixed. In this case, the device 1 provided with such a fixed needle may first of all be used in a projection instrument enabling the needle to strike the skin of the patient at a speed for the projection and a travel for the piercing depths necessary for producing a sufficient incision to make a drop of liquid sample L, for example blood, emerge on the surface of the skin, and then for retracting the needle at a controlled speed. Then the device 1 can be used to take the liquid sample L thus obtained, by means of the first end 6 of the channel 2.

Figure 15:
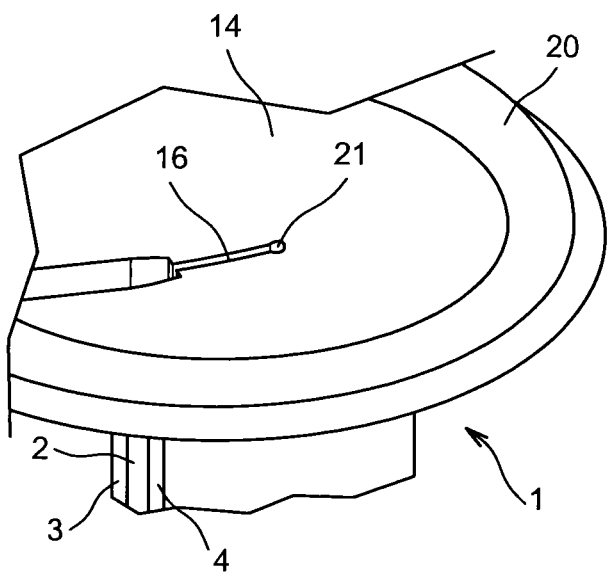
FIG. 15 illustrates a variant embodiment of the piercing means of the device of FIGS. 13A and 13B.

FIG. 15 illustrates a variant embodiment of the device in FIGS. 13A and 13B. In this example, the piercing means 21 is situated at one end, in particular a central end, of the flow opening 16 (being in particular situated in the flow opening 16) rather than at a distance from the flow opening 16, as shown in FIGS. 13A and 13B. The positioning of the piercing means 21 relative to the flow opening 16 can be chosen so as to assist the collection of liquid L in the flow opening 16 after piercing.

Figure 16:
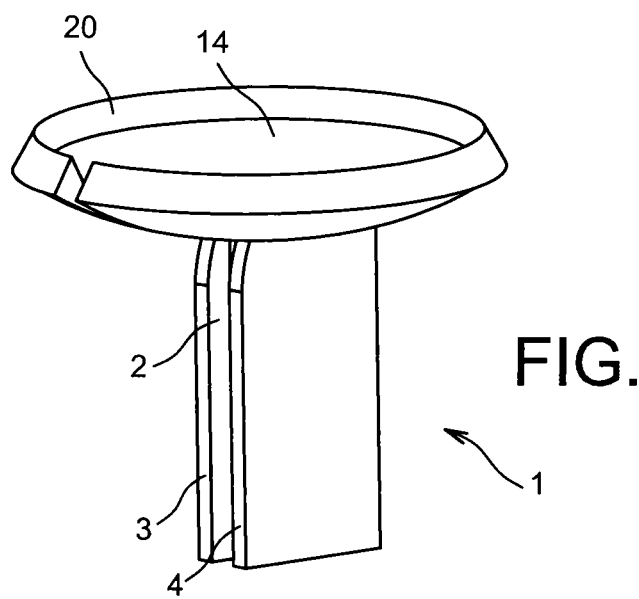
FIG. 16 shows another example embodiment of a device according to the invention, comprising a support surface.

FIG. 16 shows a variant embodiment of the device 1 according to the invention comprising a support surface 20.

In this example, the support surface 20 is no longer in the form of a circular torus as in FIGS. 13A and 13B, but in the form of a ridge projecting on the contact surface 14, enabling the body element, in particular a finger, to bear on the periphery of the sampling zone of the body element.

In the examples in FIGS. 13A, 13B and 16, the support surface 20 is circular. In a variant, the support surface 20 may also be elliptical. Whatever the case, the form of the support surface 20 can be chosen so as to conform to the body element from which the bodily fluid L is extracted.

Another example embodiment of a sampling device 1 according to the invention has moreover been shown with reference to FIGS. 17A, 17B and 18A to 18D.

More precisely, FIG. 17A shows an example embodiment of a device 1 according to the invention with a height H of the channel 2 that is variable, FIG. 17B is a partial view in cross section along B-B of the device 1 in FIG. 17A, and FIGS. 18A to 18D show a modelling of the flow of a liquid L over time, respectively during four steps, in the channel 2 of the device 1 in FIG. 17A.

In this embodiment, the height H of the channel 2 increases in a first portion P1 of the channel 2, this first portion P1 being situated between a first distance D1 and a second distance D2 with respect to the first end 6. In addition, the height H of the channel 2 decreases in a second portion P2 of the channel 2, this second portion P2 being in particular situated between the second distance D2 and the second end 7 of the channel 2 where the blocking means 9 is situated.

In particular, in this example and in no way limitatively, the first distance D1 is zero so that the first portion P1 extends from the first end 6 as far as the second distance D2 measured from this first end 6.

Moreover, preferentially, in the first portion P1, the channel 2 follows a concave form so that a segment joining two points on the channel 2 is not necessarily included in this channel 2. This concave form may allow a rapid increase in the height H of the channel 2.

The first portion P1 extends as far as the second end 7.

In the example shown in FIGS. 17A and 17B, the second distance D2 corresponds substantially to two thirds of the distance DT separating the first end 6 from the second end 7.

On the first portion P1, the height $h_1$ of the lower part 11 of the channel 2 is constant, while the height $h_2$ of the upper part 12 of the channel 2 increases gradually according to the distance with respect to the first end 6. In particular, close to the first end 6, the channel 2 extends in a concave direction.

It has in fact been found that such a concave form, close to the first end 6, allows better filling of the channel 2.

FIGS. 18A to 18D show the modelling of the flow of the liquid L in the channel 2 of the device 1 of FIGS. 17A and 17B, in the course of four steps. In these figures, the direction of flow of the liquid L has been shown by the arrow $E_c$.

It is thus possible to view the change in the interface I between the liquid L and the air A in the channel 2 of the device 1. Thus, as described previously with reference to FIG. 12B, the tangent T to the interface I, at the anchoring ridge 13, forms a large angle Δ with respect to the normal N to the anchoring ridge 13. As explained previously, this limits the formation of air bubbles.

Moreover, the increase in the height H of the channel 2 as described previously may advantageously make it possible to provide a large optical measuring zone 15, for example with a width $I_m$ of a few millimetres, for example between 3 and 4 mm. This optical measuring zone 15 is for example situated between the first portion P1 and the second end 7, as shown in FIG. 17A.

Naturally the invention is not limited to the example embodiments that have just been described. Various modifications can be made thereto by a person skilled in the art.

The expression "comprising a" must be understood as being synonymous with "comprising at least one", unless the contrary is specified.

The invention claimed is:

1. A device for taking a sample of liquid by capillarity, comprising:
   a channel for flow of the sample of liquid delimited by two internal walls of the device between which a channel bottom extends, a distance separating the two internal walls decreasing in a first direction of the channel bottom,
   the channel extending in a rectilinear direction between a first end, open onto outside of the device and configured to receive the sample of liquid, and a second end, to enable the sample of liquid to flow by capillarity along the channel bottom from the first end towards the second end,
   the channel comprising, at the second end, a first blocking means configured to block a flow of liquid in the channel from the first end towards the second end, and
   the channel comprising, on a top side of the channel below a channel upper surface of the channel, a second blocking means configured to block a flow of liquid in the channel in a second direction from the channel bottom to the upper surface of the channel and,
   wherein:
   the second blocking means comprises at least one first blocking ridge extending in the rectilinear direction, formed on each of the two internal walls, the at least one first blocking ridge being disposed at a same height on each of the two internal walls above the channel bottom, and forms a step in each of the two internal walls in a direction from the top side of the channel to the channel bottom, and
   the channel has a first width below the second blocking means and a second width above the second blocking means, a minimum value of the second width being greater than a maximum value of the first width.

2. The device according to claim 1, wherein the channel comprises the first blocking means in a form of a closure wall of the channel.

3. The device according to claim 1, wherein: the first blocking means comprises at least one second blocking ridge formed on at least one internal wall of the device and broadening at least part of the channel at the second end, and the second width is at least twice the first width.

4. The device according to claim 1, wherein the channel comprises the first blocking means in a form of a coating made locally hydrophobic.

5. The device according to claim 1, wherein the channel comprises the first blocking means in a form of a broadening of the channel bottom, configured to reduce capillary force applied to the sample of liquid, when the sample of liquid progresses towards the second end.

6. The device according to claim 1, wherein the channel is divided into at least a lower part, the channel bottom and an upper part so that the lower part is situated between the channel bottom and the upper part, the lower and upper parts being delimited by the two internal walls, the lower part having a capillary force greater than that of the upper part to allow a spontaneous capillary flow of the sample of liquid along the channel bottom from the first end towards the second end.

7. The device according to claim 1, wherein the two internal walls are secant to form the channel bottom at their intersection.

8. The device according to claim 1, wherein the channel comprises, on at least part thereof, at least one reagent in at least one of dry and lyophilised form.

9. The device according to claim 1, wherein a height of the channel remains constant while extending along the channel bottom from the first end towards the second end.

10. The device according to claim 6, wherein a height of the lower part of the channel is less than or equal to 5 mm.

11. The device according to claim 1, wherein the channel extends in a concave direction from the first end towards the second end.

12. The device according to claim 1, further comprising, at the first end of the channel, a contact surface enabling the sample of liquid to be taken, lying in a plane perpendicular to at least one internal wall of the device.

13. The device according to claim 12, wherein the contact surface comprises a support surface against which a body element is configured to bear for the sample of liquid to be taken.

14. The device according to claim 12, wherein the contact surface comprises a flow opening configured to emerge in the channel.

15. The device according to claim 1, wherein the two internal walls of the device are produced from a transparent or translucent material.

16. The device according to claim 1, further comprises piercing means to enable a skin to be pierced to collect the sample of liquid.

17. The device according to claim 1, wherein height of the channel is variable, increasing at least over a first portion of the channel.

18. The device according to claim 17, wherein the channel comprises a concave part, extending over a second portion lying between a first distance and a second distance with respect to the first end of the channel.

19. A method for analyzing a sample of liquid taken by a device according to claim 1, wherein the device is subjected to analysis means configured to analyze liquid contained in the channel at at least one predetermined analysis zone of the channel.

20. A device for taking a sample of liquid by capillarity, comprising:
a channel for flow of the liquid delimited by two internal walls of the device between which a channel bottom extends, a distance separating the two internal walls decreasing in a first direction of the channel bottom,
the channel extending between a first end, open onto outside of the device and configured to receive the sample of liquid, and a second end, to enable the liquid to flow by capillarity along the channel bottom from the first end towards the second end,
the channel comprising, at the second end, a first blocking means configured to block a flow of liquid in the channel from the first end towards the second end, and
the channel comprising, on a top side of the channel below a channel upper surface of the channel, a second blocking means configured to block a flow of liquid in the channel in a second direction from the channel bottom to the upper surface of the channel,
wherein the channel comprises a lower part and an upper part, the lower part having a bottom portion with a dihedron shape having a half-angle a, the liquid having an angle θ of contact with the two internal walls on the lower part, the lower part having a width d, the upper part having a width w1 where the upper part meets the lower part, the upper part having a width w2 greater than width w1 at an upper surface of the channel and a height H, and the two internal walls in the upper part having an angle of inclination of β with respect to a bottom to top direction of the channel and a length L in a third direction from where the upper part meets the lower part to the upper surface, wherein the following relations hold:

$H = L \times cos\ \beta,$ $w_2/(2L+(w_1-d)) < cos\ \theta,$ and $H < (w_1 cos\ \beta(1-cos\ \theta)+d\ cos\ \beta cos\ \theta]/\ [2(1-sin\ \beta)).$ 21. A device for taking a sample of liquid by capillarity, comprising:
a channel for flow of the sample of liquid delimited by two internal walls of the device between which a channel bottom extends, a distance separating the two internal walls decreasing in a first direction of the channel bottom,
the channel extending between a first end, open onto outside of the device and configured to receive the sample of liquid, and a second end, to enable the sample of liquid to flow by capillarity along the channel bottom from the first end towards the second end,
the channel comprising, at the second end, a first blocking means configured to block a flow of liquid in the channel from the first end towards the second end, and
the channel comprising, on a top side of the channel below a channel upper surface of the channel, a second blocking means configured to block a flow of liquid in the channel in a second direction from the channel bottom to the upper surface of the channel,
wherein the channel comprises a lower part and an upper part, the lower part having a bottom portion with a dihedron shape having a half-angle a, the liquid having an angle θ of contact with the two internal walls on the lower part, the lower part having a width d, the upper part having a height H, and the two internal walls in the upper part having an angle of inclination of β with respect to a bottom to top direction of the channel and a length L in a third direction from where the upper part meets the lower part to the upper surface, wherein the following relations hold:

$$(H/d) > \frac{1}{2}((1/cos\ \theta) - 1).$$

* * * * *